United States Patent [19]
Schoess

[11] Patent Number: 6,014,896
[45] Date of Patent: Jan. 18, 2000

[54] REMOTE SELF-POWERED STRUCTURE MONITOR

[75] Inventor: Jeffrey N. Schoess, Buffalo, Minn.

[73] Assignee: Honeywell Inc., Minneapolis, Minn.

[21] Appl. No.: 09/241,452

[22] Filed: Feb. 2, 1999

Related U.S. Application Data

[60] Division of application No. 08/690,263, Jul. 24, 1996, which is a continuation-in-part of application No. 08/298,686, Aug. 31, 1994, abandoned.

[51] Int. Cl.[7] .................................................. G01H 1/00
[52] U.S. Cl. ........................................................... 73/583
[58] Field of Search .............................. 73/587, 801, 583, 73/802; 340/665, 870.16; 364/508; 310/328

[56] References Cited

U.S. PATENT DOCUMENTS

| | | | |
|---|---|---|---|
| 3,239,678 | 3/1966 | Kolm ........................................ | 310/319 |
| 4,524,620 | 6/1985 | Wright et al. ............................. | 73/587 |
| 4,634,917 | 1/1987 | Dvorsky et al. ......................... | 310/328 |
| 4,685,335 | 8/1987 | Sato et al. ................................. | 73/660 |
| 4,868,447 | 9/1989 | Lee et al. .................................. | 310/328 |
| 4,894,787 | 1/1990 | Flannelly et al. ........................ | 364/508 |
| 5,184,516 | 2/1993 | Blazic et al. .............................. | 73/799 |
| 5,300,875 | 4/1994 | Tuttle ....................................... | 320/20 |
| 5,383,133 | 1/1995 | Staple ...................................... | 364/508 |

*Primary Examiner*—Richard A. Moller
*Attorney, Agent, or Firm*—John G. Shudy, Jr.

[57] ABSTRACT

An acoustic rotor monitor that is an autonomous self-powered measurement instrument which can detect embedded and hidden fatigue cracks in remotely inaccessible devices such as helicopter rotor system components. A predictive maintenance-related problem for rotor craft is the detection of fatigue cracks as a continuous real-time monitoring process under dynamic rotor system loading conditions. The rotor monitor focuses on the embedding an acoustic emission-based smart sensor directly into the rotor system to measure the high frequency stress waves indicating that a structural crack has propagated as a "self-powered" measurement without reducing structural integrity.

6 Claims, 16 Drawing Sheets

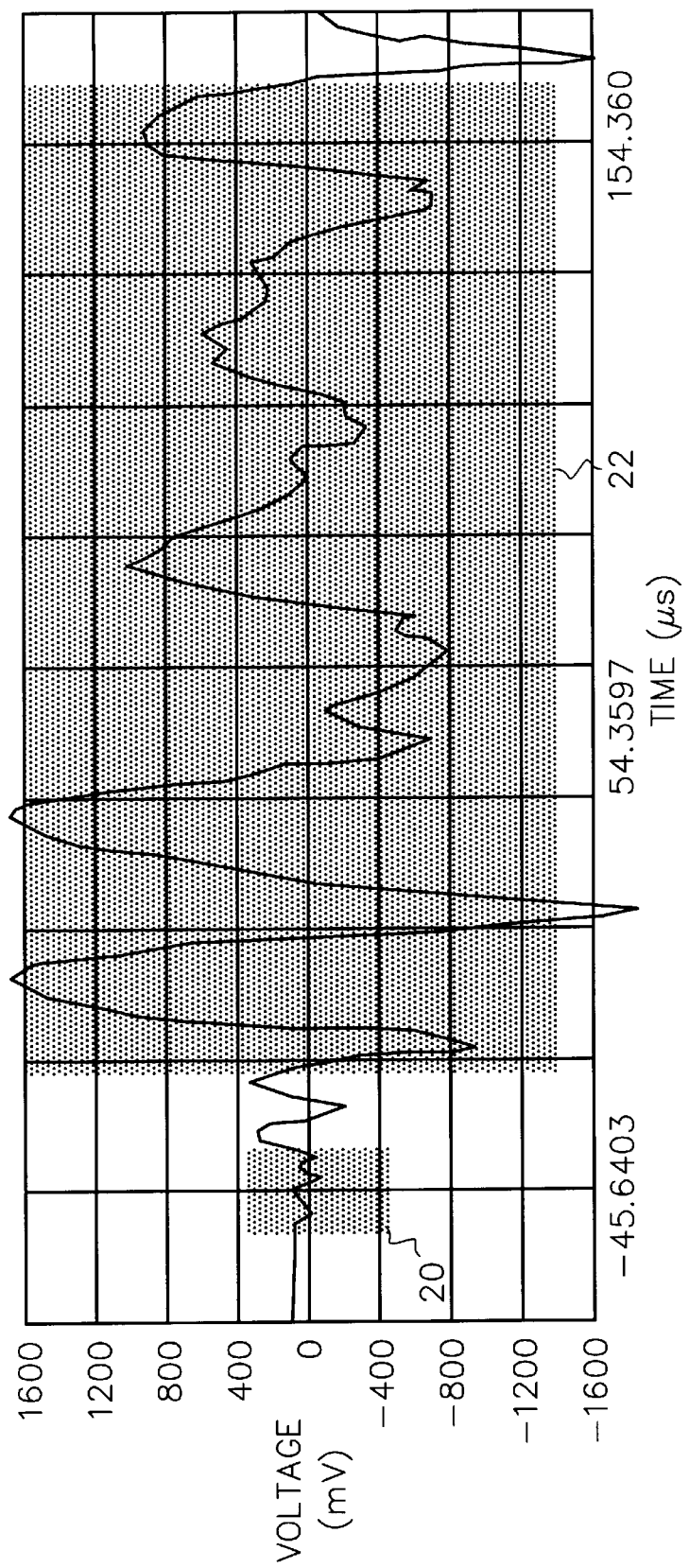

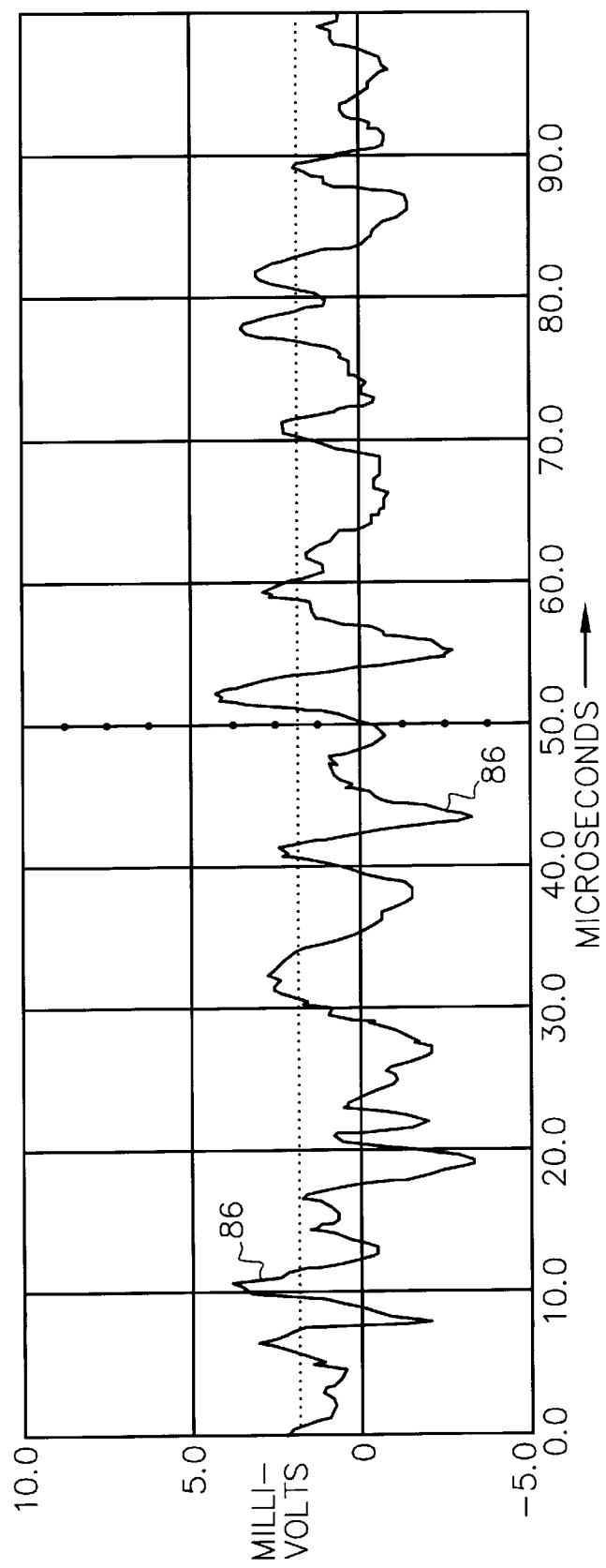

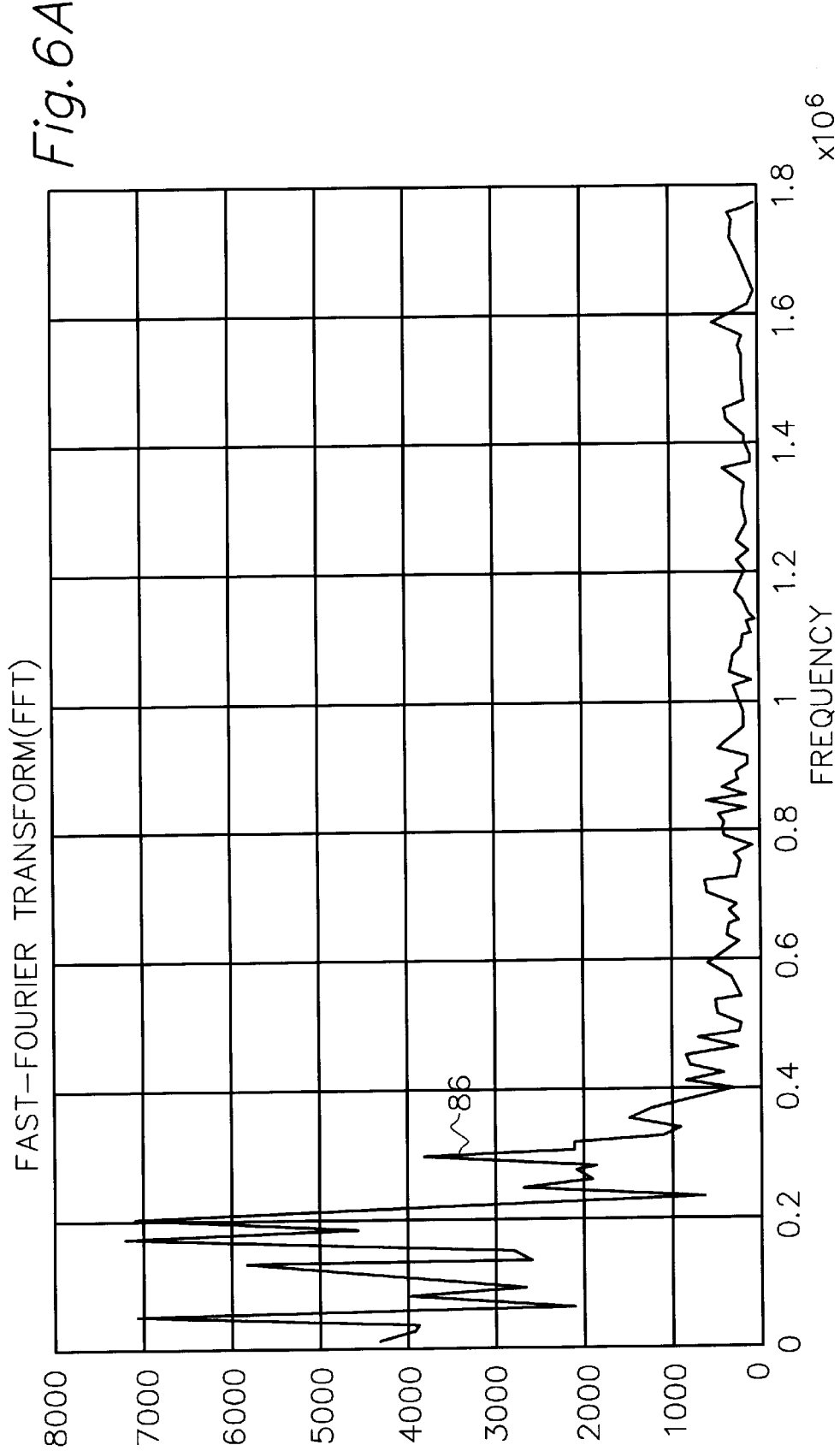

REMOTE SELF-POWERED STRUCTURE MONITOR

This is a Divisional application my co-pending application Ser. No. 08/690,263, filed Jul. 24, 1996, which in turn was a continuation-in-part of my application Ser. No. 08/298,686, filed on Aug. 31, 1994 abandoned.

FIELD OF THE INVENTION

The invention pertains to remote sensors and particularly real-time remote sensors. More particularly, the invention pertains to real-time remote devices for monitoring the integrity of inaccessible and/or moving structures.

BACKGROUND OF THE INVENTION

Real-time monitoring of fatigue cracks and stress corrosion cracks in helicopter rotor heads is a difficult task. Such cracks are a significant problem for rotor systems on helicopters. Class "A" Helicopter mishaps have risen at an alarming rate in the last decade. A class A mishap is defined as the loss of a vehicle (i.e., a rotor craft). From 1980 to 1990, almost half of the mishaps were due to class A failures. Recent British studies performed by the Helicopter Air worthiness Review Panel (HARP) indicated that 33 percent of the accident mishaps were caused by a main rotor failure leading to loss of life and aircraft. An additional 25 percent of mishaps due to main rotor problems caused the aircraft to be ditched at sea.

The inventor and his employer have been studying the effects of metal fatigue on commercial transport and military aircraft. Working directly with a major airline and as a major subcontractor in a U.S. Air Force smart metallic structures program, the inventor has learned that real-time structural health monitoring for aircraft involves an additional dimension of complexity beyond the conventional nondestructive evaluation (NDE) techniques for detecting structural integrity problems such as fatigue cracking and hidden corrosion. Structural integrity inspection is typically localized to rotor head hub assemblies, bearings, connection linkages, and tie bars.

In a typical rotor, each blade has three distinct bearings (commonly called hinges) at its hub end, allowing movement in the feathering, flap, and lead/lag axis. The hinges may incorporate metal ball-races, or an elastometric bearing made of synthetic rubber to minimize rotor head vibration effects. Fatigue cracks occur in highly loaded rotor head components. These rotor components are susceptible to corrosion cracking in such environments as moist sea air, sea water and acid rain. The rotor head components experiencing fatigue cracks include the main rotor hub, the connecting link, the pitch shaft, the tie bar and pin, the pitch housing, the lag dampers, the forward and aft rotor drive shafts, and the blade fittings. Fatigue cracks occur in the ball-races of the main rotor hub, the rotor hub spline area, the pivot area of connecting links, the individual laminates of the tie bar assembly, the tie bar pin, the inspection access holes on the aft rotor drive shaft, damper attachment points, and the blade fitting.

Several NDE methods are available to detect metallic-related fatigue cracks, but each method has one or more significant technical limitations. These detection methods include visual, tap test, ultrasonic, eddy current, and x-ray radiography. Visual inspection is appropriate for checking surface conditions such as cracks in the main hub body or general surface corrosion but is not effective for detecting cracks within the ball-races of the main hub assembly. A low-frequency eddy current can detect cracks in rotor system components but requires an extensively trained NDE technician to properly position the eddy current probes and interpret test results. X-ray radiography can be used but requires special equipment, and limits general maintenance crew access to the aircraft while the X-ray testing is being performed. Each of these NDE methods also has two significant drawbacks. First, some mechanical disassembly of the helicopter rotor is required which increases operational costs and limits flight availability time. Second, such methods are not real-time health monitoring solutions which can provide an early warning indication of a structural crack initiation or crack propagation event.

SUMMARY OF THE INVENTION

The present invention, that is, the rotor acoustic monitoring system (RAMS), incorporates the concept of embedding an acoustic emission-based smart sensor directly into a rotor system to measure the stress waves in real-time to detect rotor system structural fatigue cracks. A key technical requirement is the detection of structural cracking in a rotor head component during rotor operation to provide an early warning indication of crack growth. The rotor monitor is directly attached to the rotor component to measure crack initiation and propagation, prior to reaching a flight critical crack length, which could lead to catastrophic failure or loss of aircraft.

The present rotor monitor has various advantages over the related art. The invention incorporates a piezoelectric AE transducer which provides a "dual-use" function which includes a high fidelity stress wave acoustic emission transducer to detect structural crack growth and to generate self-contained electrical power using externally applied vibration energy. The piezoelectric polyvinylidene fluoride (PVDF) based transducer design detects high frequency (1–10 MHz) stress wave acoustic emission energy which directly correlates with the detection of structural crack initiation and propagation. The remote and self-powered rotor monitor incorporates an integral self-contained power generator by applying an external mechanical stress to the PVDF piezoelectric film by a inertial load generated by the mass of attached, internal lithium batteries.

BRIEF DESCRIPTION OF THE FIGURES

FIG. 3 is a graph of stress wave characteristics associated with a structural event.

FIG. 5 shows a stress wave due to a structure under stress.

FIGS. 6a and 6b reveal a fast-Fourier transform equivalent of a stress wave.

DESCRIPTION OF THE PREFERRED EMBODIMENT

Figure 1:
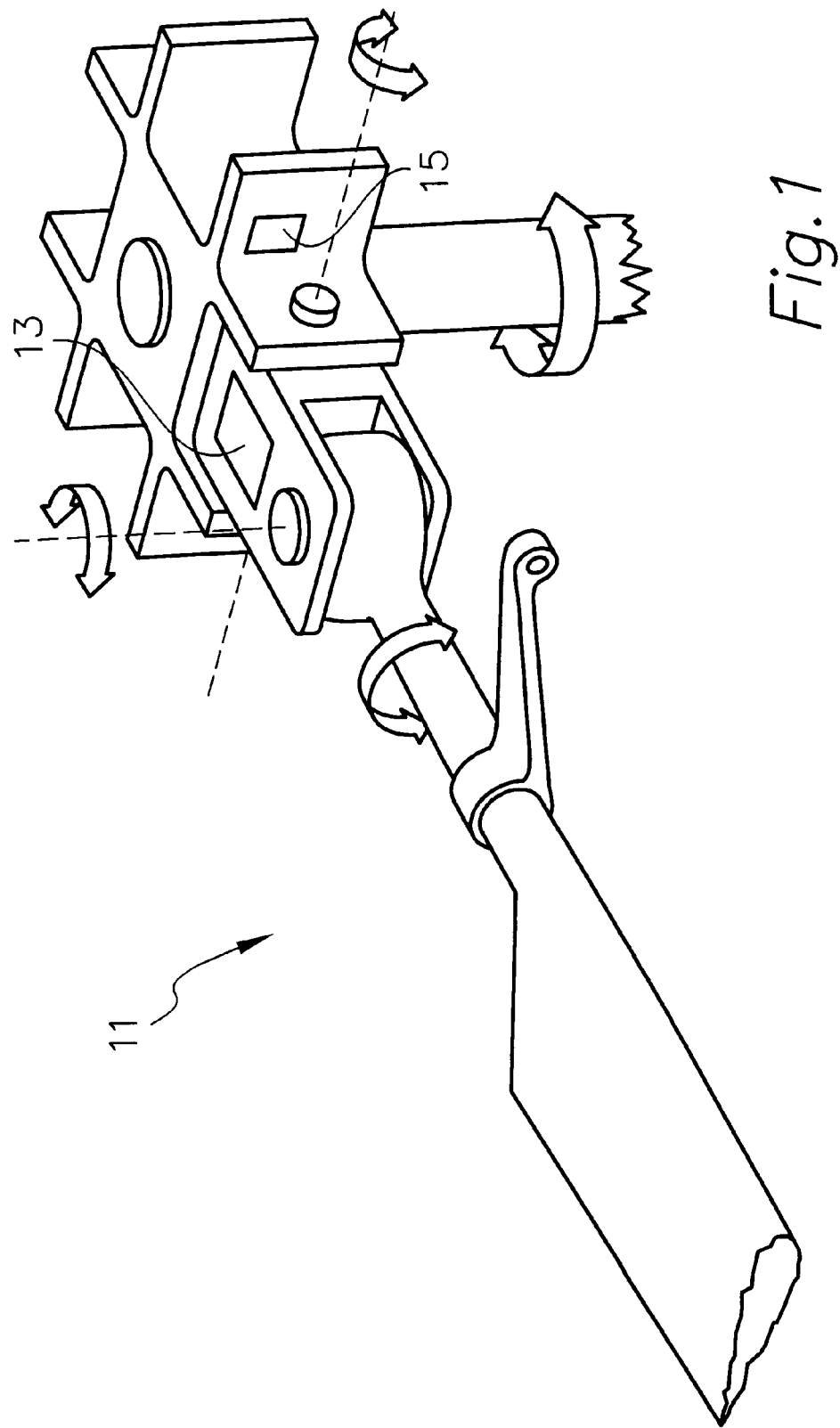
FIG. 1 is an example device on which the present invention is used.
Figure 2:
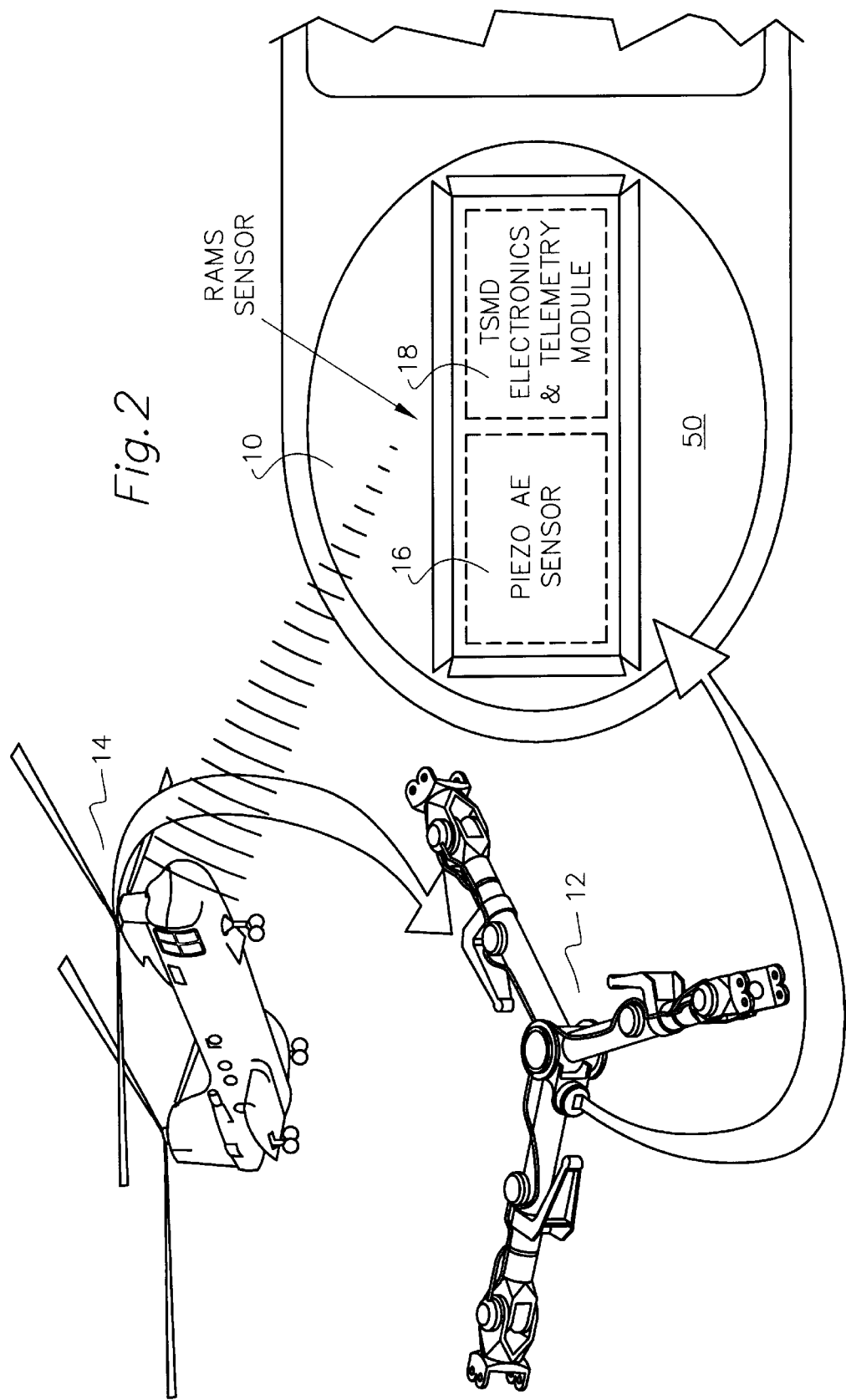
FIG. 2 illustrates application of the rotor monitor.

The overall rotor monitor concept, for rotors 11 like that of FIG. 1, is illustrated in FIG. 2 which shows an acoustic emission-based smart sensor 10 mounted on a rotor system 12 component of a craft 14, to detect rotor system structural cracks as a "self-powered" measurement. Sensor 10 may be mounted, for instance, at location 13 or 15.

Rotor monitor 10 of FIG. 2 incorporates embedding an acoustic emission (AE) sensing element 16 and electronics 18 into a conformal PEEL N' STICK (by Honeywell Inc., Minneapolis, Minn.) surface mount package on surface 50. One feature of the rotor monitor 10 is the measurement of acoustic sound in an aircraft structure, such as rotor 12 of aircraft 14, for determining whether a structural fatigue crack has been initiated or is propagating. Such crack phenomena reduce the aircraft's structural integrity and/or its ability to support an aerodynamic load.

Acoustic emission (AE) is a high frequency stress wave which originates from and is caused by local redistribution of stresses within the aircraft structure (i.e., the growth of a crack). Rotor monitor 10 applies AE technology which is being developed for aging aircraft applications in a smart metallic structures program, referred to as "stress wave AE" which is based on a plate wave theory.

The stress wave energy propagates through a structure as a waveform with specific velocity and modal characteristics. The potential of a catastrophic structural failure occurring depends on several design-related parameters including the physical shape and geographical location of the structural component in question, its age and exposure to corrosive elements, and the stress-level environment (i.e., aerodynamical loading). If a crack exists in a flight-critical structural component, the length of the crack and crack propagation rate are key parameters of interest. In a U.S. Air Force fixed wing aircraft, a crack length of 0.5 inch can lead to a catastrophic failure.

FIG. 3 illustrates an actual "stress wave" structural AE event recorded the smart structure laboratory of the inventor's employer, which demonstrates the detection of a metallic crack growth. The AE test was performed on a 3"×10" high-tensile metal test coupon and was fatigue-loaded to fracture in a holding vise. The two-dimensional plot reveals an unusual shape with two stress wave characteristics, that is, an extensional (in-plane component) mode 20 and an flexural (out-of-plane component) mode 22 of the waveform. Extensional mode 20 arrives first, and exists at a much higher frequency than flexural mode 22. Extensional mode 20 data helps in detecting structural failures related to composites delamination and metal fatigue in tension-compression (in-plane) loaded situations. Flexural mode 22 data indicates the effects of composites micro-cracking and metal fatigue due to impacts and metal flexure.

Figures 4A, 4B:
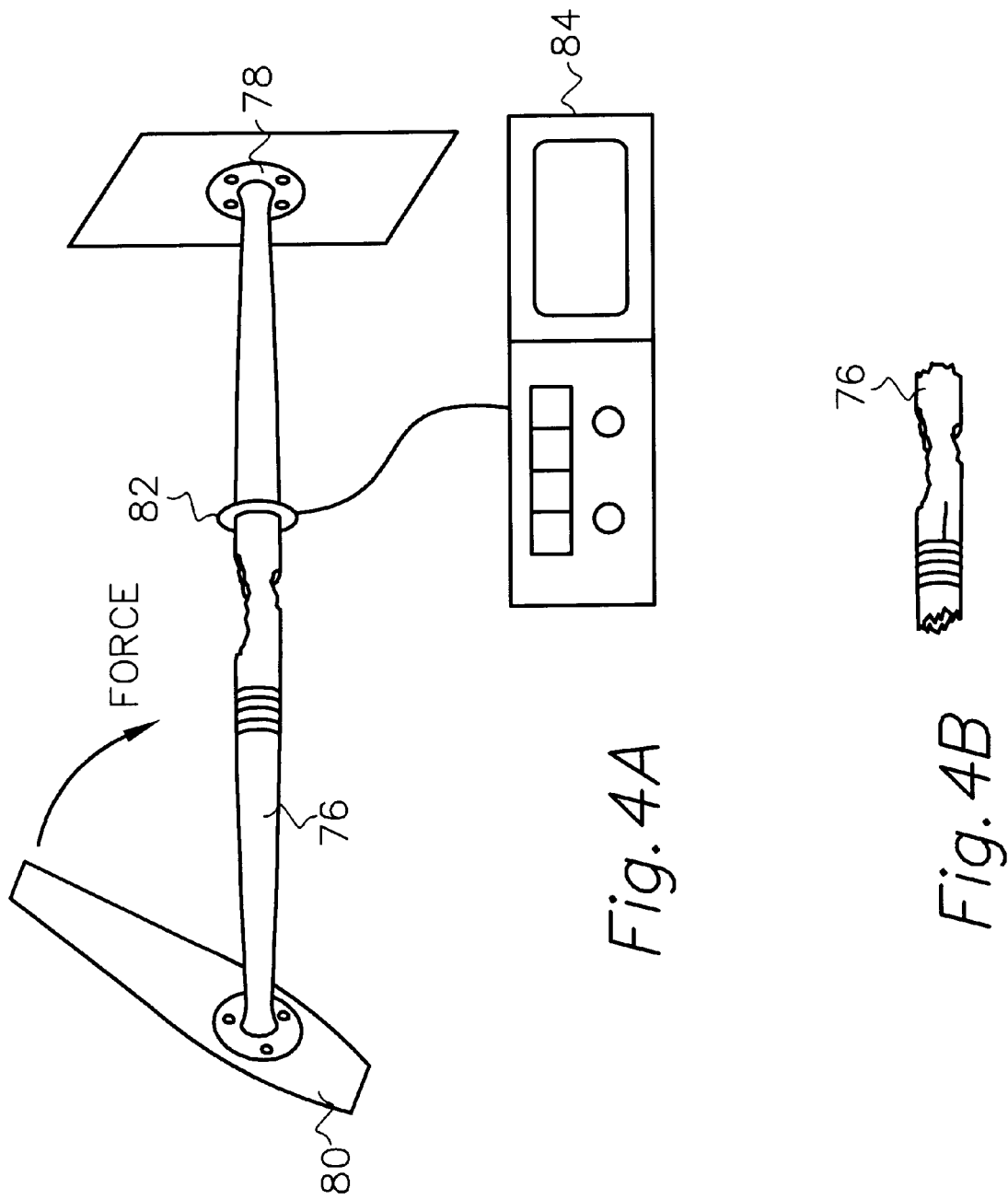
FIGS. 4a and 4b illustrate monitoring of a structure under stress.

The inventor and his employer performed a proof-of-concept H-46 rotor structural fatigue test at its smart structure laboratory. An H-46 aircraft is a U.S. Navy twin rotor helicopter. The key focus of this effort was to demonstrate the overall rotor system health monitoring concept of detecting fatigue crack growth using stress-wave acoustic emission technology. FIG. 4a illustrates a simulated H-46 rotor component, a rotor drive shaft 76, which has a form factor similar to a rear rotor drive shaft located on the Navy H-46 helicopter. The rotor component 76 is shown rigidly attached on one end 78 and mounted to a composite lever arm assembly 80 at the other end. An axial load of 2,000 ft-lbs of force is applied to rotor shaft 76 to stress the shaft.

FIG. 4a also illustrates a detailed view of the test instrumentation setup with a high bandwidth off-the-shelf acoustic emission (AE) transducer 82 (HARISONICS G0504) attached using a plastic cable tie and acoustic coupling compound to characterize the acoustic stress-wave effects. The AE transducer 82 signal was measured and recorded by a high-speed storage oscilloscope 84 for detailed analysis. FIG. 4b illustrates the fatigue crack located in the middle of the rotor shaft with some rotor material removed. The rotor fatigue test invoked a crack growth sequence which resulted in a total propagation of 1.0 inch starting to the left of the crack tip point (two vertical scribed marks).

Figure 6B:
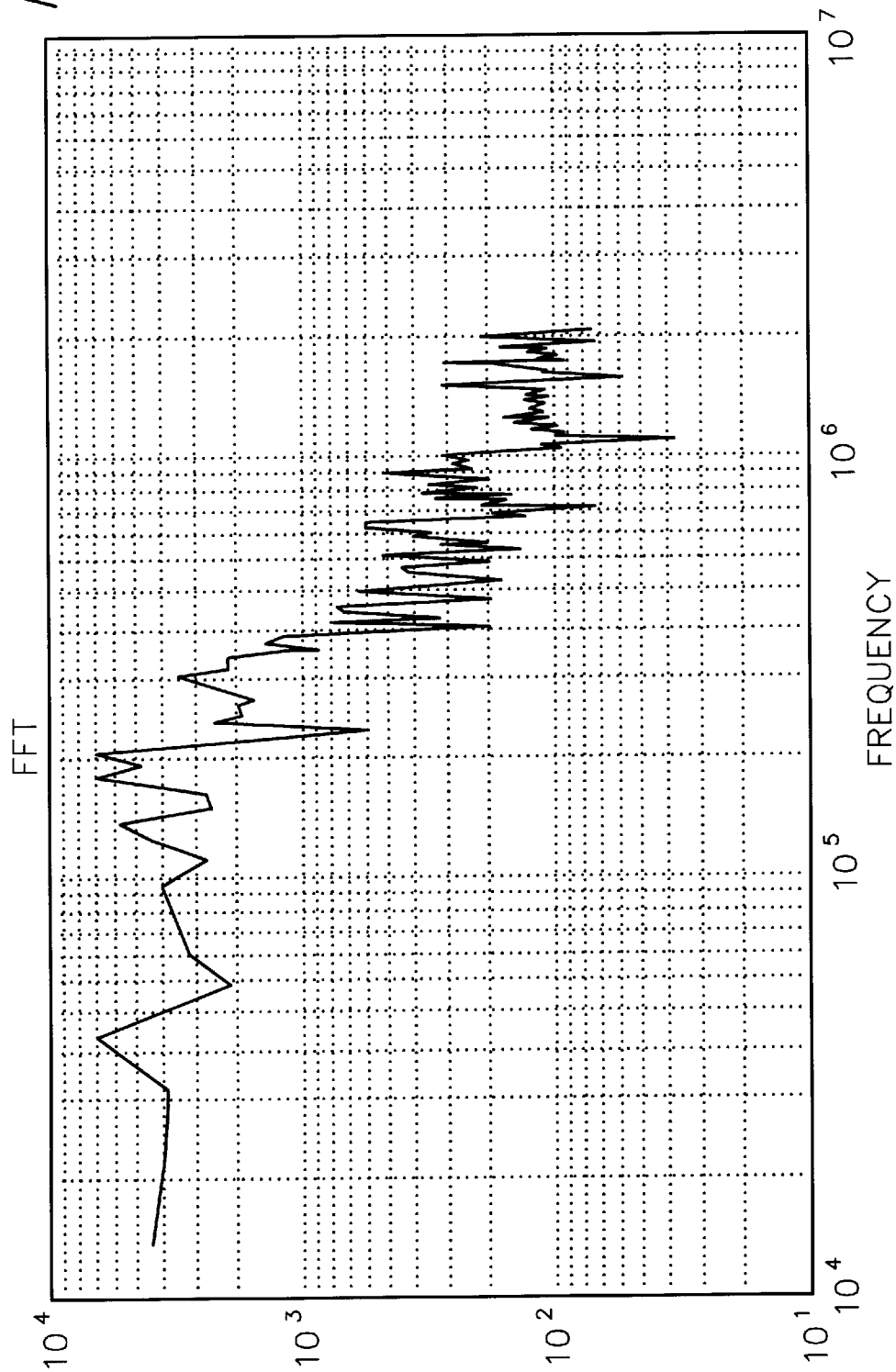
Figure 6C:
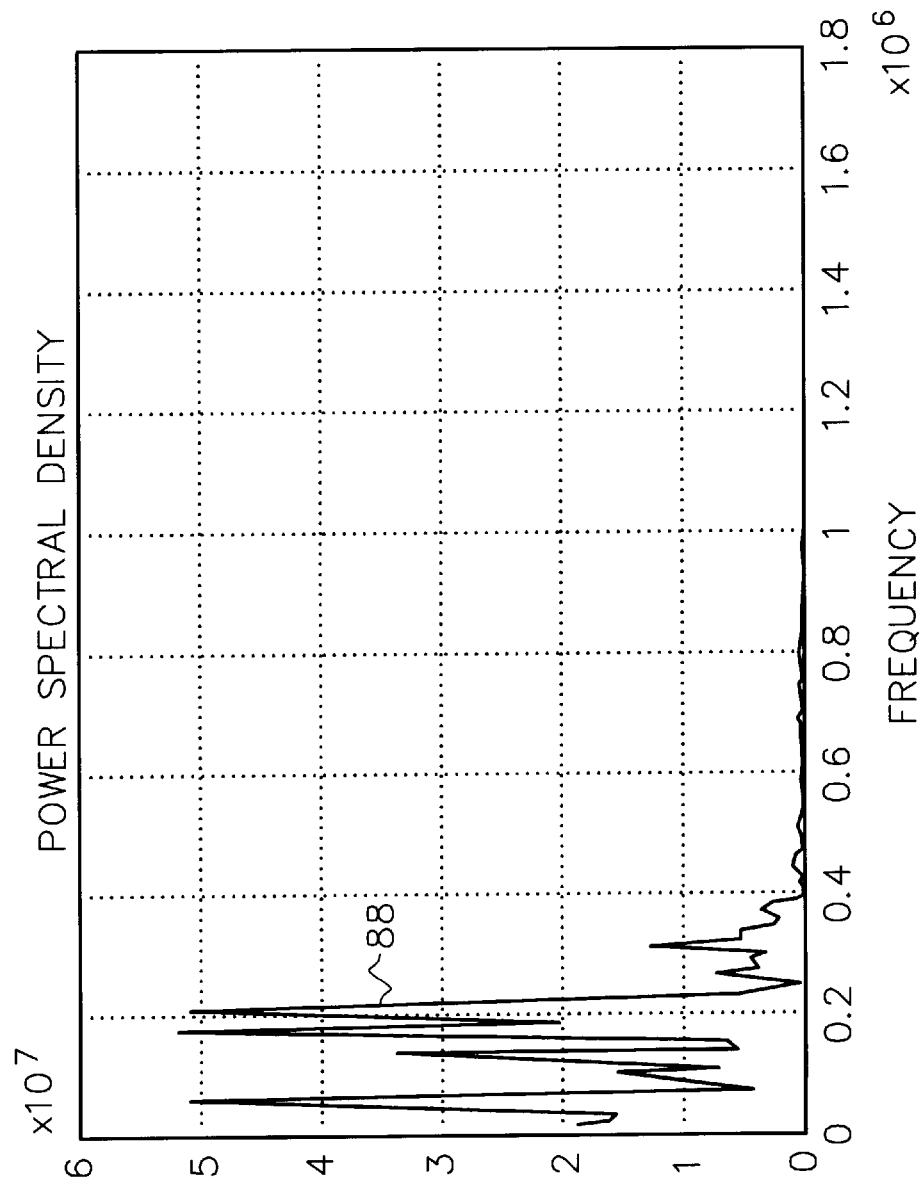
FIGS. 6c and 6d reveal a power spectral density of a stress wave.
Figure 6D:
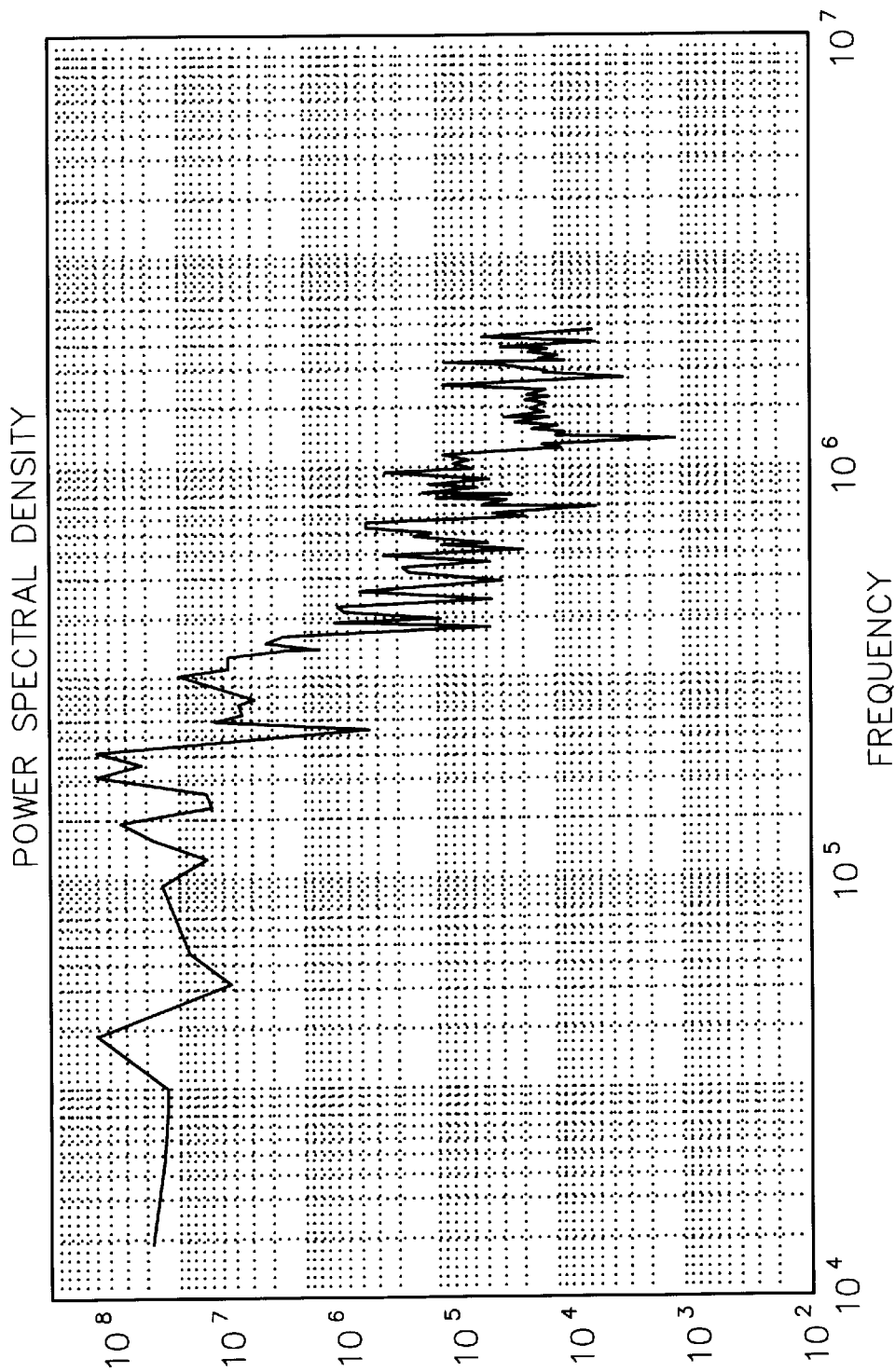

A typical AE crack event recorded during the test is shown illustrated in FIG. 5. Waveform 86 highlights a robust high-frequency stress wave with a peak-to-peak amplitude of 7.5 millivolts and fundamental frequency of 267 kHz and higher frequency components extending out to greater than 600 kHz. The Fast-Fourier transform (FFT) equivalent 88 of this waveform 86 is shown in FIGS. 6a and 6b while the power spectral density (PSD) 88 of energy content is illustrated in FIGS. 6c and 6d. The numbers to the left (ordinate) of the graphs of FIGS. 6a–d are normalized numbers or ratios. The normalized numbers are linear in FIGS. 6a and 6c and logarithmic in FIGS. 6b and 6d. The data results involve a frequency rolloff of 60 db/dec., a 3 db corner frequency of 210 kHz, and frequency components of 67 kHz, 100 kHz, 178 kHz, 200 kHz, 255 kHz, 300 kHz, 375 kHz and 600 kHz (at −40 db).

Conclusions derived from research on stress wave AE, directly applicable to rotor monitor 10 design, are the following items. Metallic cracking structural events occur at very high frequencies (0.2–10 MHz), well out of the operating range of conventional helicopter 14 noise due to mechanical and aircraft flow effects (DC to 200 kHz), making stress wave AE analysis a viable tool for detecting potential structural failures and crack growth. The ability to predict catastrophic structural failures depends on accuracy of tracking the growth of a crack and relating the crack size to structural integrity loss. While performing design analysis work, the inventor has learned that a structural crack will grow to a critical length of 0.25 inch while releasing AE energy (up to 100 discrete AE related (i.e., crack related) events in a one second time interval) into the structure of interest.

Figure 7:
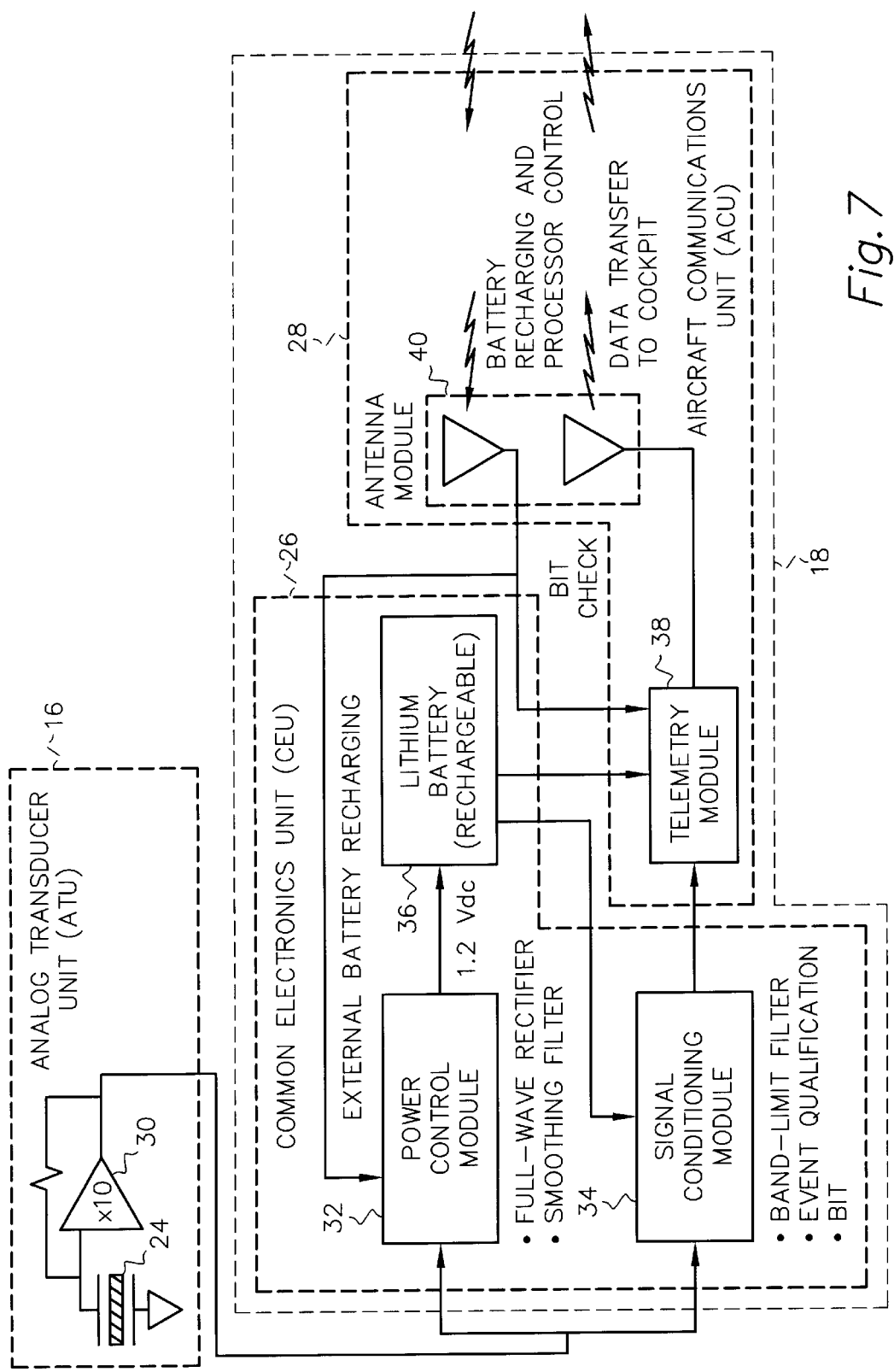
FIG. 7 is a schematic of the monitor electronics.
Figure 8:
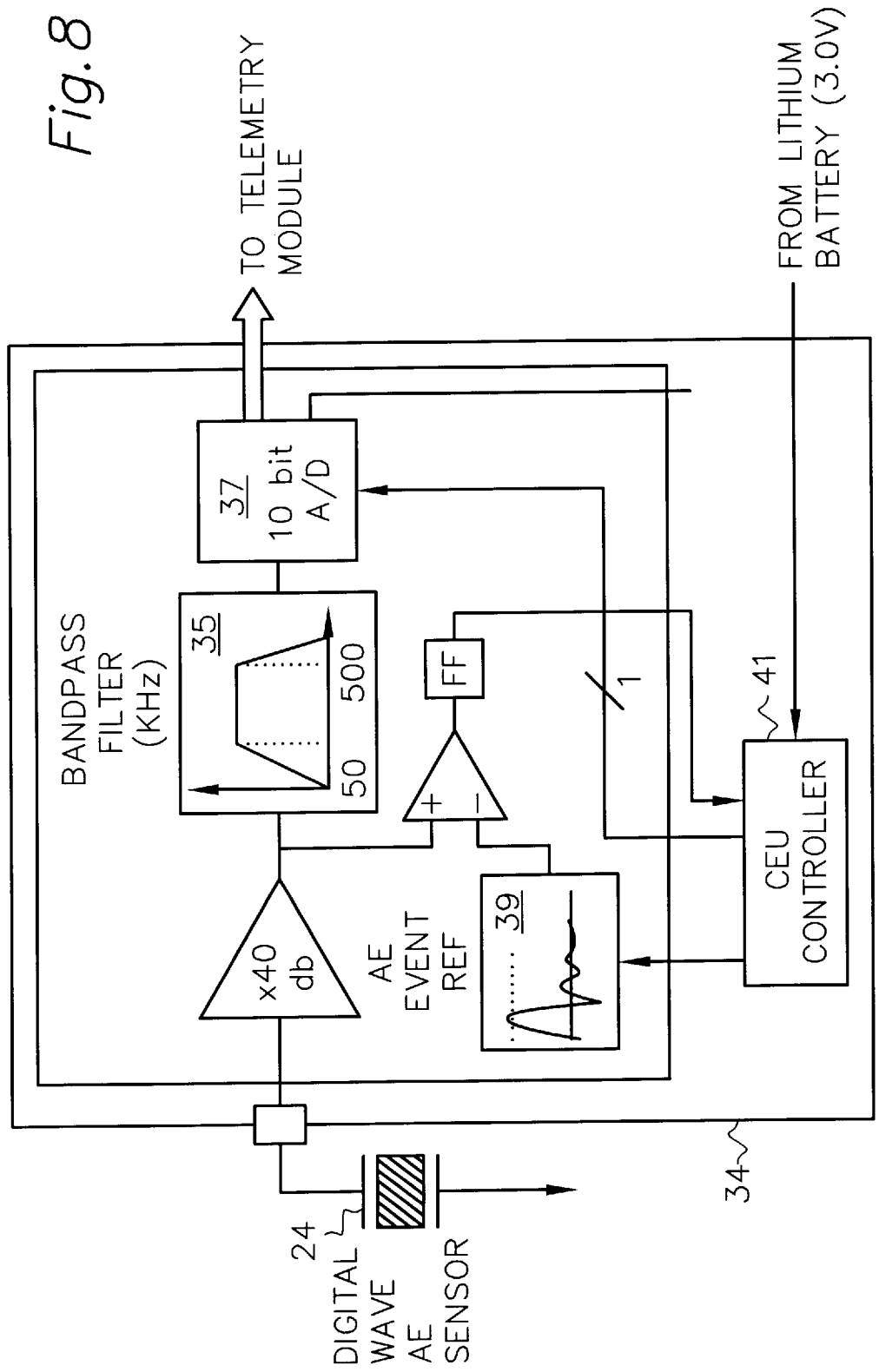
FIG. 8a is a diagram of a signal conditioning circuit.

Electronics 18 of rotor monitor 10, as shown in FIG. 7, is partitioned into three sensor management functional building block units. The units are analog transducer unit (ATU) 16, common electronics unit (CEU) 26 and aircraft communications unit (ACU) 28. ATU 16 contains AE piezo film transducer assembly 24 and signal amplifiers 30. CEU 26 incorporates a cost-effective "common electronics" digital core including power management control 32, signal conditioning module 34, and integral rechargeable lithium battery cell 36. A detailed diagram of the signal conditioning module 34 as shown in FIG. 8 highlighting an active bandpass filter 35 having corner frequencies of 50 kHz and 500 kHz, respectively, a 10-bit analog-to-digital converter (A/D) 37, AE event qualification circuitry 39 and a CEU microcontroller 41. Event qualification circuit 39 operates as a low-power comparator function which compares an AE event reference 39 signal with the raw AE signal to enable data acquisition. ACU 28 contains a low power telemetry module 38 and integral full duplex antenna 40 to facilitate rotor head crack growth data retrieval and non intrusive external battery recharging.

CEU core 26 of FIG. 7 is the "intelligence" of the rotor monitor, which is able to make sensor-related decisions. CEU 26 provides five levels of sensing capability including data conversion, conversion of physical phenomena acoustic emission to a measurable electronic signal, environmental compensation to correct for changes in the operating environment, local data qualification to interpret and qualify the sensor data as being relevant to the health monitoring problem, and communications to provide an standardized interface for data retrieval and analysis.

Rotor monitor 10 electronics 18 includes a dual-use piezo AE transducer 24 to detect crack growth anomalies and provide secondary power generation. The present approach is to detect crack growth as an acoustic emission (AE) structural event. Stress wave AE analysis is an application of AE technology which offers significant advantages over conventional threshold-event detection (i.e., counting the AE events related to a structural event based on a fixed threshold) AE technology. These advantages include excellent helicopter operational noise immunity, direct compatibility with existing rotor systems, wide dynamic range (0.2 to 10 MHz) and highly quantitative crack growth anomaly information.

Studies have shown that most of fixed and rotary wing aircraft noise spectrum, due to airflow, and mechanical vibration, is limited to 100–200 kHz (i.e., 3 db point). The stress wave approach has the advantage of operating at 1.0–10 MHz, an order of magnitude above the operational noise spectrum. In addition, the stress wave AE approach features excellent crack event detection by directly quantifying crack growth as a stress event with in-plane and out-of-plane displacement modes of operation.

The dual-use approach proposed for measuring stress wave AE is based on the application of PVDF, a piezoelectric polymer film technology. PVDF is used for measuring stress wave AE crack growth activity. PVDF is a commercially available material, manufactured by Amp, Inc., in Valley Forge, Pa., with thicknesses from 9 to 110 $\mu$m. PVDF has been successfully used as a stress wave AE transducer material for monitoring fiber-matrix disbonds and delaminations in fibrous composite materials. A PVDF film transducer has several advantages over conventional piezoelectric transducers. Its physical flexibility allows easy conformance to curved surfaces. The size and shape of the transducer can be tailored for a specific application. The application of PVDF film results in a low manufacturing cost. The low mass of PVDF film does not drastically affect the mechanical response of the helicopter component and minimizes the effects of centrifugal forces in debonding sensor assembly 24 from rotor 12 as well. PVDF film has high sensitivity to out-of-plane displacements of the structure surface when bonded to the surface with an appropriate adhesive.

Figure 9:
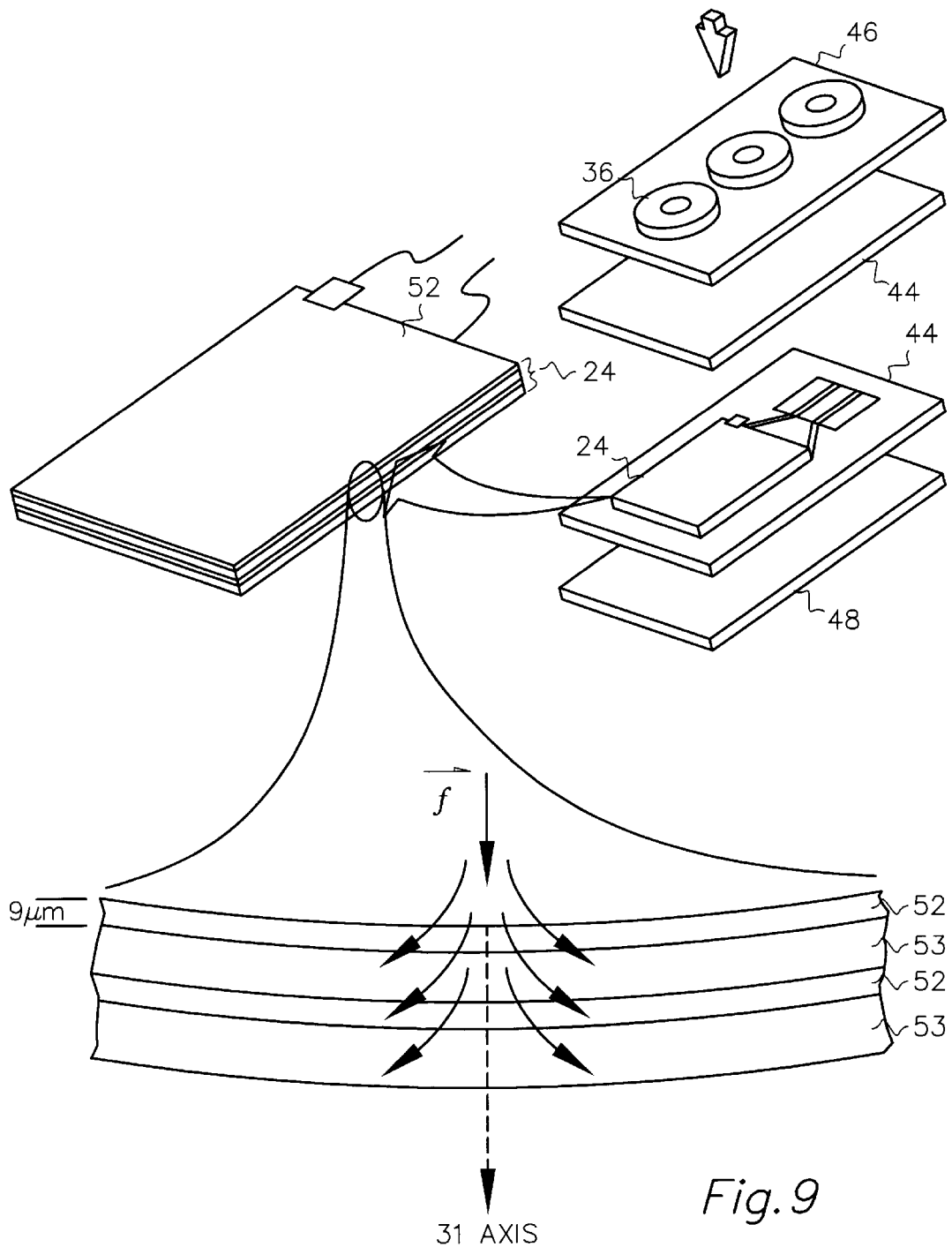
FIG. 9 shows the piezo film structure sensor and power generator.

FIG. 9 illustrates a low-risk piezo-based transducer 42 design. The low risk design features the piezo transducer element 24 (Amp, Inc., part no. LDT2-028k with physical dimensions of 2¾"×½") sandwiched between rubber pads 44 and aluminum 46/polymer 48 substrate plates clamped together. Polymer substrate 48 material (i.e., polyimide) provides mechanical relief support while assuring conformity with helicopter component surface 50. FIG. 5 also shows three rechargeable lithium batteries 36 located on top of aluminum plate 46. Lithium batteries 36 on AE transducer 24, function as an inertial load to stress the PVDF film and to generate a voltage potential which can serve as secondary power source when excited by rotor head 12 component vibrations. The power generated by piezoelectric film is proportional to the equation $$\text{Power(watts)} = \int dw = 1/2 \frac{Q^2}{C} = 1/2\, C \times V_0^2, \text{ where}$$

W=work performed to transfer Q (charge)
C=capacitance of piezofilm ($\mu$f)
$V_o$=voltage output of film due to applied stress (volts) and
$V_o = g_{xx} \chi_n xt$
$g_{xx}$=piezo stress constant in axis of stress applied $$is \left( \frac{V/m}{N/m^2} \right)$$

N=number of layers
$\chi_n$=applied stress
t=film thickness (micrometers)

The electromechanical coupling factor of the piezo film is about 15 percent at 100 Hz making it an ideal power generator for rotor head 12 applications.

The measurement of AE crack growth data in a rotor system 12 without slip rinds is achievable with the present invention which is an autonomous "self-powered" device. Rotor monitor 10 has a fault-tolerant dual-element power source having a low-power lithium-based rechargeable battery 36 as a primary power supply source and a piezoelectric generator 24 activated by rotor head 12 vibrations as a secondary power supply source. The piezoelectric device is for "dual-use" device, as a high fidelity stress wave acoustic emission transducer to detect rotor crack growth and to be an integral power generator.

A single layer of piezoelectric film 52 provides for self-powered operation proportional to the applied external stress (i.e., force applied), the piezofilm capacitance and piezo stress constant. Piezofilm 52 is attached to a rotor head 12 component such as a rotor system lead/lag damper, on a surface 50. Piezo element 52 is stressed mechanically in the Z-axis, i.e., axis 31. A stack of piezo film or layers 52 with elastomeric layers 53 between layers 52, and between the closest piezo layer 52 and surface 50 to be monitored, constitutes a multi-layer transducer 24. The elastomeric layer provides two key functions of electrically isolating individual piezo layers and transferring force applied from the 31 axis to the 33 axis. The mechanical coupling of the elastometric layer permits the idea of combining the stress (force) in both the 33 and 31 axes to maximize power generation potential. The power generated by each piezo layer is proportional to the combined effect of piezo stress constants in each axis or:

$$\text{Power(watts)} = \tfrac{1}{2} C \times V^2_{o31} + \tfrac{1}{2} C \times V^2_{o33}$$

or $$= \tfrac{1}{2} C \times (g_{31} \times \chi_n \times t) + \tfrac{1}{2} (g_{33} \times \chi_n \times t)$$

Figure 10:
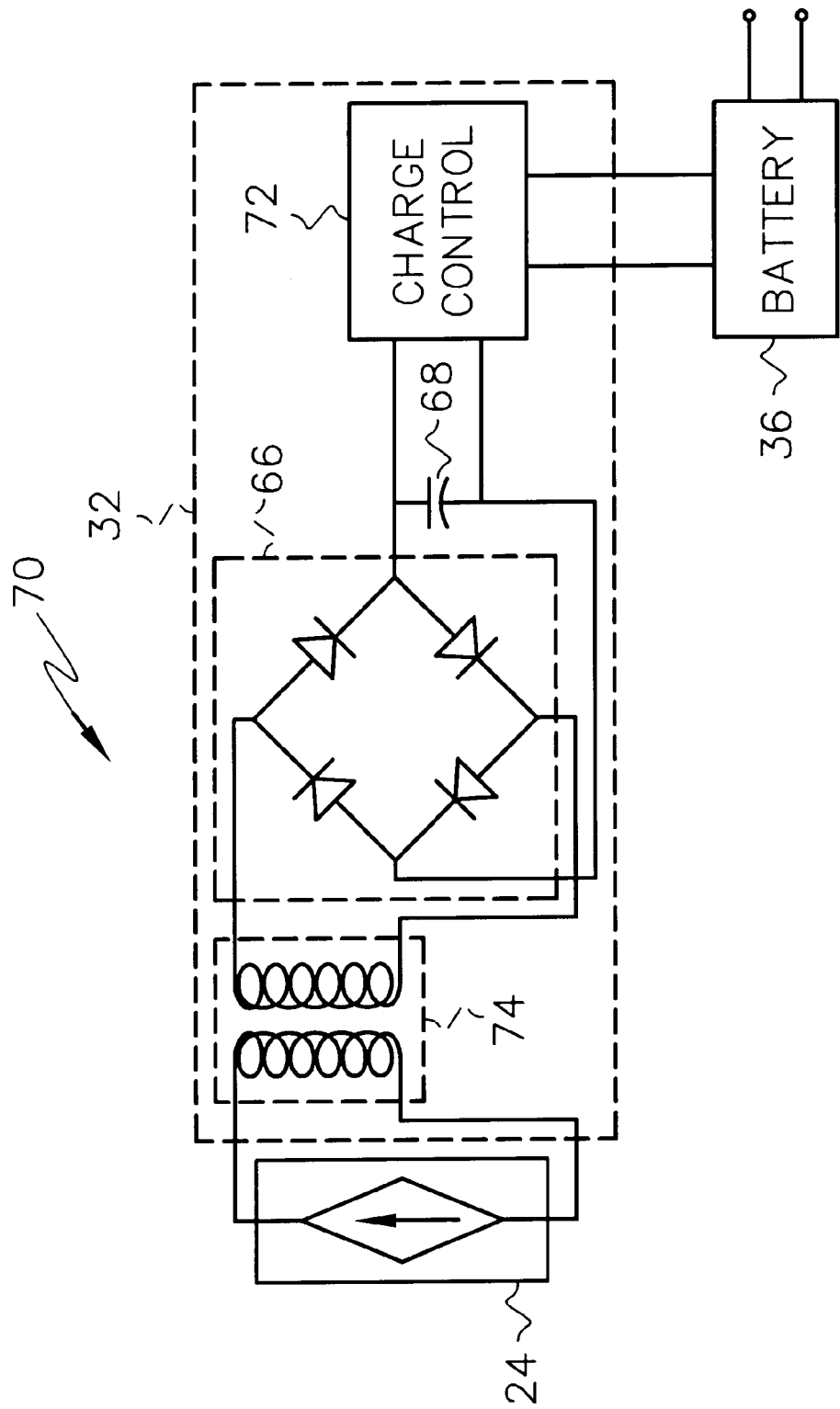
FIG. 10 is a diagram of the piezo film sensor electronics.

As the film 52 flexes, (transducer 24) each piezofilm layer generates an electrical voltage proportional to the applied stress in the 31 axis and the voltages are summed together as an equivalent "series" electrical circuit (series circuit of voltage sources). FIG. 10 shows power generation electronics 70. Current from transducer 24 may go through a transformer 74 or an amplifier 30 of FIG. 4. The current goes to the primary of a three volt-ampere step-down transformer 74 (having a 12:1 primary/secondary winding ratio) or amplifier 30 to a full-wave rectifier (FWR) circuit 66. The step-down transformer converts the piezofilm output from high voltage, low current to a lower voltage, higher current output. Rectifier 66, which is within the rotor monitor electronics module 18, converts the energy from alternating current (AC) to direct current (DC), and stores the energy in a double electric layer capacitor 68 (i.e., super cap NEC part no. FAOH303), having a nominal value of 0.03 farad, and/or the rechargeable lithium battery 36 system, via a charge control circuit 72. An available off-the-shelf power control 32 integrated circuit (IC) 72, for example, a model BQ2003 fast charge IC by Benchmarq, Inc., of Carrolton, Tex., controls the energy delivery rate.

The power generated by the piezo film transducer 24 can be calculated, for example, on a U.S. Navy H-46/SH-60 helicopter. According to the NAVAIR 01-1A-24 U.S. Navy Aviation Vibration Analysis Manual, at Station no. 477 of the aft rotor head, the fuselage body vibration is 0.757 inches/sec in the vertical direction and 0.872 inch/sec in the lateral direction, corresponding to axes 31 and 33, respectively.

Figure 11:
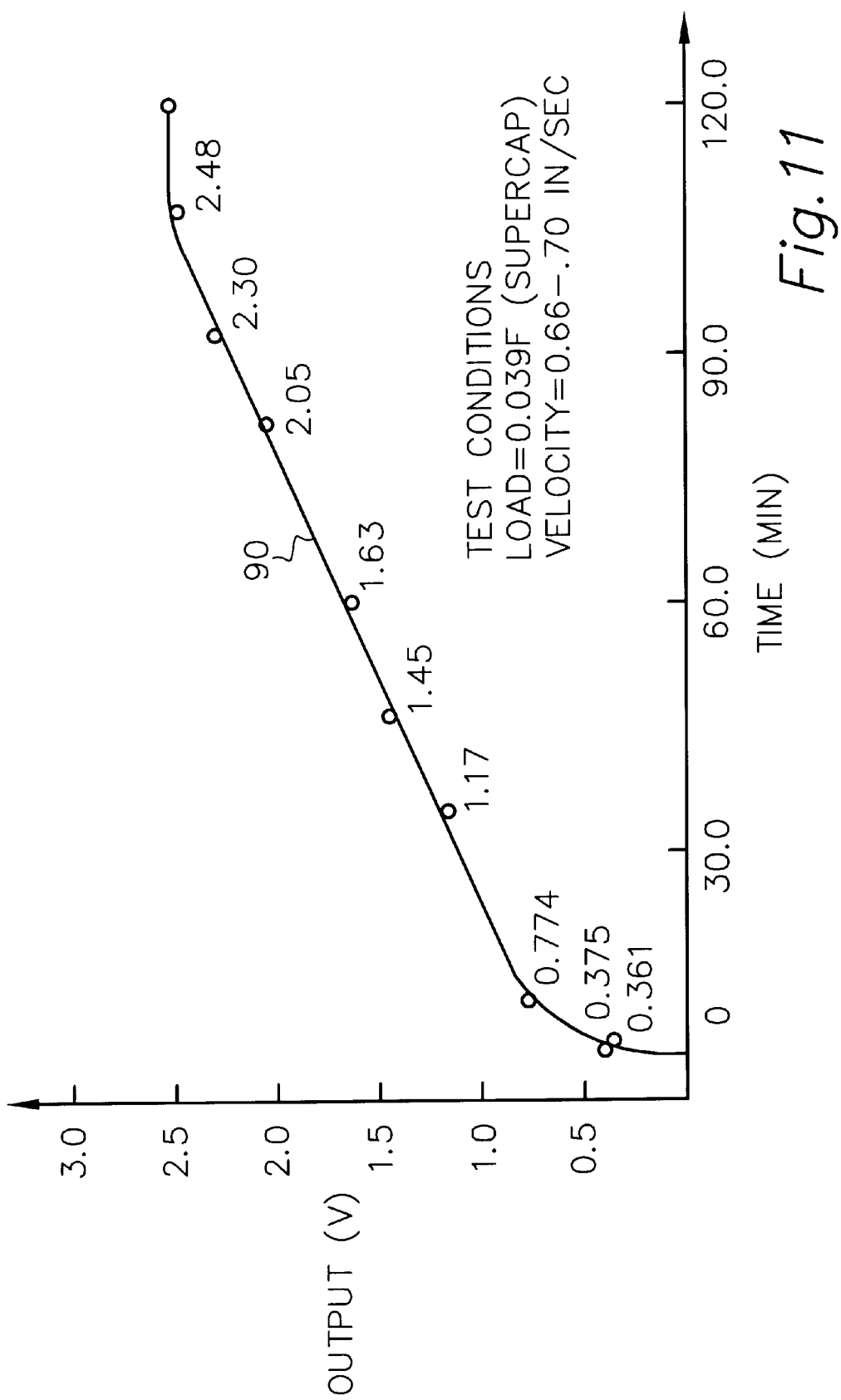
FIG. 11 is a graph of the output of the piezo film sensor.

Preliminary power generation test results have been generated in a smart structure laboratory of the inventor's employer to verify and validate the self-powered design concept. Under H-46 helicopter 14 rotor 11 simulated structural loading conditions (velocity range of 0.66–0.70 in/sec) a single layer of piezofilm (with physical dimensions of 2¾"×½") has demonstrated a power generation potential greater than 5.0 milliwatts. Curve 90 of FIG. 11 illustrates the actual test data recorded in charging a super capacitor of 0.039 farad from 0.0 to 2.5 volts over a time period of 100 minutes. The piezo film transducer was mounted on a flexible test coupon with dimensions of 3¾"×2¼" and excited in a cantilever mode on a vibration tester table to generate the results.

Battery 36 is a rechargeable lithium polymer battery manufactured by SEIKO Instruments. It features a high operating voltage of 3.3 volts compared to 1.2 volts for conventional NiCad batteries). The lithium polymer battery has almost 3 times the storage capacity of conventional NiCad batteries of the same size. The model SL621 battery has a capacity of 0.2 mAh, a diameter of 6.8 mm and weighs 0.2 grams. The average power consumption of rotor monitor 10 is about 1–5 milliwatts.

Figure 12:
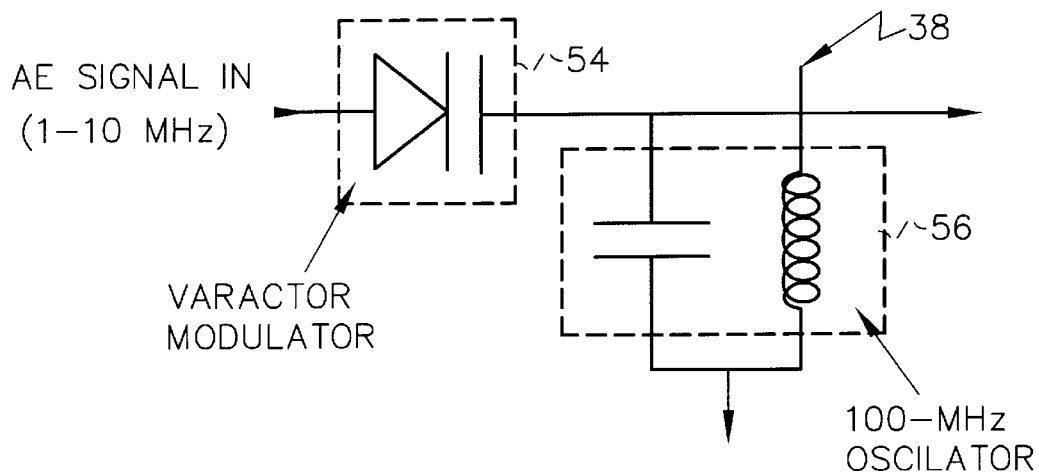
FIG. 12 reveals a wireless telemetry circuit.

The retrieval of the AE crack growth data is based on a ultra low power frequency modulated (FM) technique. FIG. 12 illustrates the basic components of wireless FM telemetry module system 38. Module 38 includes a varactor modulator circuit 54 and a high frequency carrier oscillator 56. Module 38 is connected to antenna 58 of module 40 in FIG. 13. Varactor modulator 54 accepts the 1–10 MHz AE crack data as an input and modulates it on top of an FM carrier frequency of 88 to 108 MHz from oscillator 56. Varactor 54 operates on the principle of a capacitance bias shift at the varactor output being proportional to the applied AE signal. The power dissipation of this commercially available design is very low (50–100 $\mu$a) and has excellent noise immunity.

Figure 13:
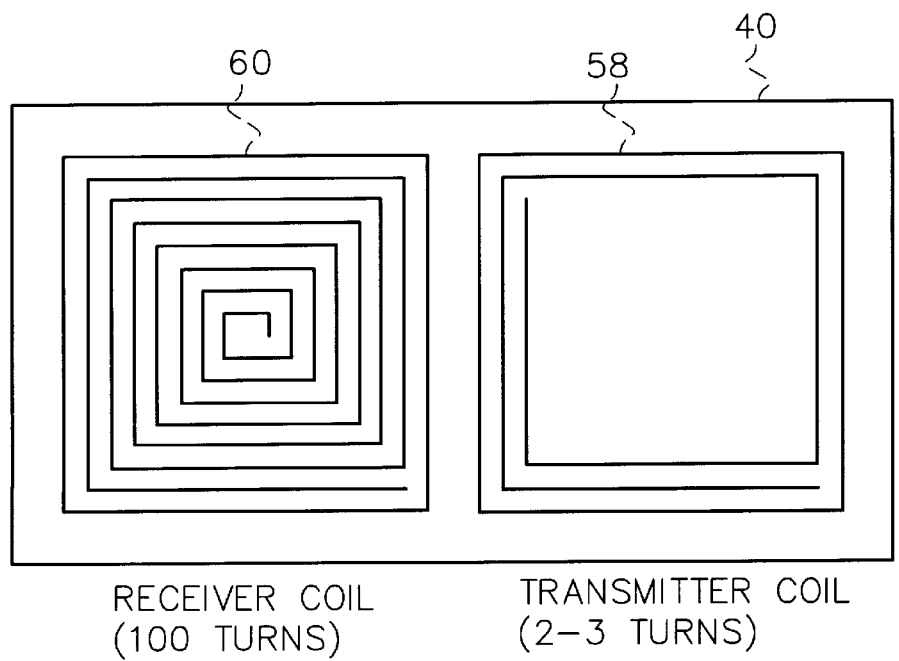
FIG. 13 shows a dual-purpose antenna.

FIG. 13 illustrates the integral dual function antenna module 40 with a dedicated transmitter coil 58 of 2–3 turns and receiver coil antenna 60 of 100 turns for external battery 36 recharging. Antenna module 40 is located in the flex circuit board assembly on a dedicated flex circuit board (FCB) layer of the multilayer board assembly. A hand-held probe with a telemetry receiver is used to capture AE data for debriefing and detailed analysis. The telemetry receiver contains a phase lock loop (PLL) receiver to demodulate the FM transmitted AE data.

In the rotor monitor 10 packaging, the piezofilm 52 AE transducer module 16 and electronics 18 are integrated together into a commercially available PEEL N' STICK package which can be easily attached to any rotor head 12 component.

Figure 14:
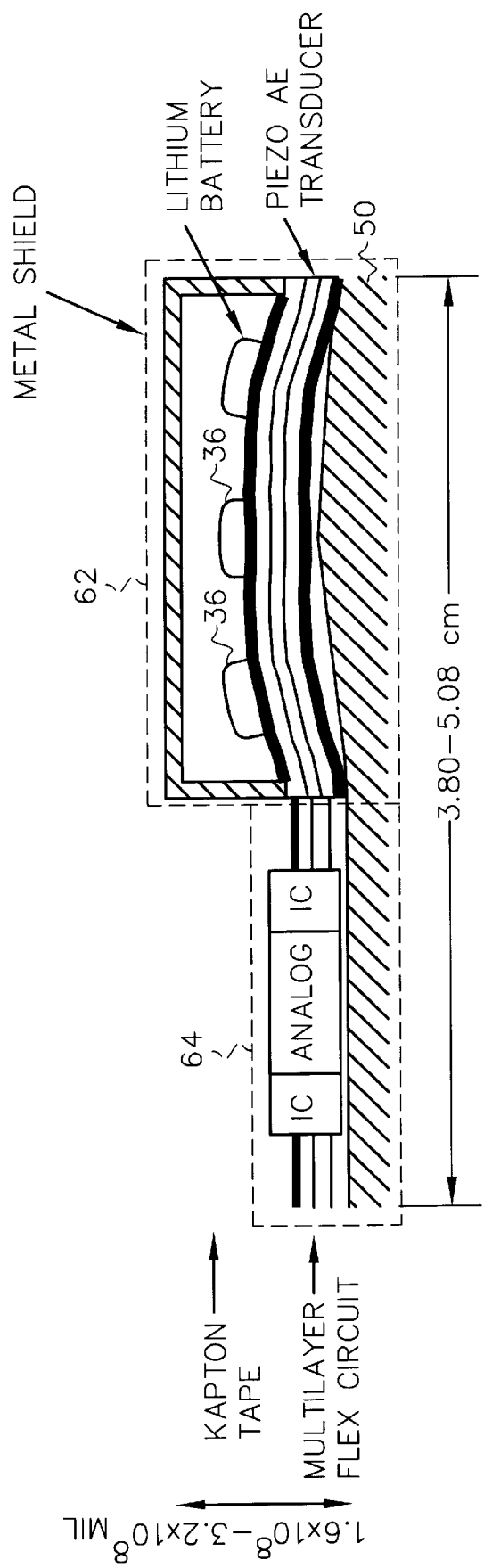
FIG. 14 is a cross-section of the rotor monitor package assembly.

FIG. 14 illustrates a detailed cross-sectional view of the rotor monitor 10 PEEL N' STICK package assembly. The pictorial highlights a simple conformal multilayer flex circuit assembly having two subassemblies, the AE piezo film transducer subassembly 62, and the rotor monitor electronics and low-power telemetry module subassembly 64.

A flexible circuit material (flex circuit board (FCB)) is used to provide a conformal package to adhere to the curved surfaces 50 of the rotor head 12 components such as the lead/lag damper or rotor hub assembly to directly monitor the crack growth process. In many FCB applications, an adhesive backing is used to minimize externally applied forces. The flex circuit has multilayer capability for the analog/digital circuits and an integral ground plane to minimize electromagnetic interference (EMI) effects. The material commonly used for FCB production is called KAPTON which is made by DUPONT. KAPTON is a low dielectric material with excellent temperature and wear properties. A KAPTON based flex circuit can withstand a wide operational temperature from –50° F. to +700° F. In addition, several high strength/high temperature adhesives are manufactured by the 3M Company in St. Paul, Minn., which are epoxy-based and feature rapid cure times which are directly compatible with FCB materials and manufacturing processes.

I claim:

1. A remote metal rotating structure monitor, comprising:
   an acoustic emission energy PVDF piezoelectric transducer mounted on a metal rotating structure to be monitored for detecting a condition of said metal rotating structure using non repetitive high frequency acoustic emission events of 1 to 10 MHz, stress wave acoustic emission energy and to generate self-contained electrical power from vibrations by said metal rotating structure;
   a signal conditioner connected to said transducer to receive stress wave acoustic emission energy therefrom and identify a signal indicative of crack propagation on said metal rotating structure;
   a power controller connected to said transducer to selectively use power from said transducer as a secondary power supply source;
   a power storage device connected to said power controller and said signal controller to receive and discharge power as determined by said power controller, said power storage device being positioned on said sensor to provide an inertial load; and
   a radio frequency telemetry circuit connected to said signal conditioner and said power storage device to transmit data from said signal conditioner identifying crack propagation and transmit power to said power storage device; and
   an antenna system connected to said telemetry circuit and said power controller to transmit said data and transmit said power;
   wherein said transducer outputs the electrical power signals due to compression, stretching and/or bending of the sensor caused by the vibration of the structure and enhanced by said inertial load.

2. The monitor of claim 1, which further includes a signal processor connected to said piezo acoustic emission transducer for receiving the electrical signals from said emission sensor.

3. The monitor of claim 2, wherein said piezo acoustic emission sensor is formed from a plurality of piezo-electric layers and a plurality of elastomeric layers situated between the plurality of piezo-electric layers, wherein said sensor outputs the electrical power signals due to compression, stretching and/or bending of the plurality of piezo-electric layers, caused by vibration of the structure.

4. The monitor of claim 3, wherein said piezo acoustic emission sensor wherein the piezo-electric and elastomeric layers are stacked on one another alternately in that one elastomeric layer is situated between adjacent piezo-electric layers.

5. The monitor of claim 4, wherein said piezo electric transducer is flexible and conformable to the structure being monitored.

6. The monitor of claim 1, wherein a single piezo acoustic emission sensor is used per structural member.

* * * * *